(12) United States Patent
Xiao et al.

(10) Patent No.: US 9,702,953 B1
(45) Date of Patent: Jul. 11, 2017

(54) METHOD OF SAMPLING IN PURE PHASE ENCODE MAGNETIC RESONANCE IMAGING

(75) Inventors: Dan Xiao, Fredericton (CA); Bruce Balcom, Fredericton (CA)

(73) Assignee: University of New Brunswick, Fredericton, New Brunswick (CA)

( * ) Notice: Subject to any disclaimer, the term of this patent is extended or adjusted under 35 U.S.C. 154(b) by 608 days.

(21) Appl. No.: 13/572,153

(22) Filed: Aug. 10, 2012

(51) Int. Cl.
| | |
|---|---|
| G01R 33/56 | (2006.01) |
| G01R 33/561 | (2006.01) |
| G01R 33/48 | (2006.01) |
| G01N 24/08 | (2006.01) |

(52) U.S. Cl.
CPC ......... *G01R 33/56* (2013.01); *G01R 33/4818* (2013.01); *G01R 33/561* (2013.01); *G01N 24/081* (2013.01)

(58) Field of Classification Search
CPC .... G01N 24/081; G01V 3/32; G01R 33/5617; G01R 33/50; G01R 33/4816; G01R 33/56; G01R 33/561; G01R 33/4818
USPC .......................... 324/300–322; 600/407–422
See application file for complete search history.

(56) References Cited

U.S. PATENT DOCUMENTS

| | | | | |
|---|---|---|---|---|
| 2005/0004448 | A1* | 1/2005 | Gurr ...................... | G01R 33/54 600/420 |
| 2006/0116828 | A1* | 6/2006 | Chen et al. .................... | 702/22 |
| 2008/0303520 | A1* | 12/2008 | Chen et al. .................... | 324/309 |
| 2011/0050223 | A1* | 3/2011 | Balcom et al. ............... | 324/307 |
| 2011/0181284 | A1* | 7/2011 | Balcom et al. ............... | 324/309 |
| 2011/0204892 | A1* | 8/2011 | Li et al. ........................ | 324/309 |

OTHER PUBLICATIONS

Paulsen, Jeffrey L., et al. "Least squares magnetic-field optimization for portable nuclear magnetic resonance magnet design." Magnetics, IEEE Transactions on 44.12 (2008): 4582-4590.*
Tang Wen, One Well Evaluation in Low Permeability Gas Sandstones from Nuclear Magnetic Resonance (NMR) Logs, Paper in SPE Middle East Unconventional Gas Conference and Exhibition, 140798-MS (2011).
Maclean O. Amabeoku, et al., Calibration of Permeability Derived from NMR Logs in Carbonate Reservoirs, Paper in SPE Middle East Oil Show, 68085-MS (2001).
G. M. Hamada, et al., Determining Petrophysical Properties of Low Resistivity Reservoirs Using Nuclear Magnetic Resonance Logs, Paper in SPE Annual Technical Conference and Exhibition, 56789-MS (1999).
Henry A. Ohen, et al., Laboratory NMR Relaxation Measurements for the Acquisition of Calibration Data for NMR Logging Tools, Paper in SPE Western Regional Meeting, 35683-MS (1996).
C. E. Morriss, et al., Hydrocarbon Saturation and Viscosity Estimation from NMR Logging in the Belridge Diatomite, Paper in SPWLA 35th Annual Logging Symposium, 1994-C (1994).
Stefan Menger, Manfred Prammer, A New Algorithm for Analysis of NMR Logging Data, Paper in SPE Annual Technical Conference and Exhibition, 49013-MS (1998).

(Continued)

*Primary Examiner* — Melissa Koval
*Assistant Examiner* — Rishi Patel
(74) *Attorney, Agent, or Firm* — Eugene F. Derényi; Fogler, Rubinoff LLP

(57) ABSTRACT

A method of sampling in pure phase encode MRI including restricting sampled points to a specified region.

10 Claims, 12 Drawing Sheets

(56) References Cited

OTHER PUBLICATIONS

M. G. Prammer, NMR Pore Size Distributions and Permeability at the Well Site, Paper in SPE Annual Technical Conference and Exhibition, 28368-MS (1994).

R. Freedman, C. E. Morriss, Processing of Data From an NMR Logging Tool, Paper in SPE Annual Technical Conference and Exhibition, 30560-MS (1995).

S. Chen, et al., Optimization of NMR Logging Acquisition and Processing, Paper in SPE Annual Technical Conference and Exhibition, 56766-MS (1999).

M. N. Miller, et al., Spin Echo Magnetic Resonance Logging: Porosity and Free Fluid Index Determination, Paper in SPE Annual Technical Conference and Exhibition, 20561-MS (1990).

Colin S. Poon, R. Mark. Henkelman, Practical T2 Quantitation for Clinical Applications, J. Maagn. Reson Imaging 2(5): 541-553, Oct. 1992.

Oliver Bieri, et al., Quantitative Mapping of T2 Using Partial Spoiling, Magn. Reson. Med. 66(2): 410-418, Aug. 2011.

O. Beuf, et al., Magnetic Resonance Imaging for the Determination of Magnetic Susceptibility of Materials, J. Magn. Reson. B 112(2): 111-118, Aug. 1996.

B. J. Balcom, Single-Point Ramped Imaging with T1 Enhancement (SPRITE), J. Magn. Reson. A 123(1): 131-134, Nov. 1996.

Linqing Li, et al., Spin Echo SPI Methods for Quantitative Analysis of Fluids in Porous Media, J. Magn. Reson. 198 (2): 252-260, Jun. 2009.

Oleg V. Petrov, et al., T2 Distribution Mapping Profiles with Phase-Encode MRI, J. Magn. Reson. 209(1): 39-46, Mar. 2011.

Oleg V. Petrov, Bruce J. Balcom, Two-Dimensional T2 Distribution Mapping in Porous Solids with Phase Encode MRI, J. Magn. Reson. 212(1): 102-108, Sep. 2011.

G. McGibney, et al., Quantitative Evaluation of Several Partial Fourier Reconstruction Algorithms Used in MRI, Magn. Reson. Med. 30(1): 51-59, Jul. 1993.

G. J. Marseille, et al., Nonuniform Phase-Encode Distributions for MRI Scan Time Reduction, J. Magn. Reson. B 111(1): 70-75, Apr. 1996.

Andrew V. Barger, et al., Time-Resolved Contrast-Enhanced Imaging with Isotropic Resolution and Broad Coverage using an Undersampled 3D Projection Trajectory, Magn. Reson. Med. 48(2): 297-305, Aug. 2002.

Michael Lustig, et al., Sparse MRI: The Application of Compressed Sensing for Rapid MR Imaging, Magn. Reson. Med. 58(6): 1182-1195, Dec. 2007.

Meghan Halse, et al., Centric Scan SPRITE Magnetic Resonance Imaging, J. Magn. Reson. 165(2): 219-229, Dec. 2003.

Alexandre A. Khrapitchev, et al., Sectoral Sampling in Centric-Scan SPRITE Magnetic Resonance Imaging, J. Mang. Reson. 178(2): 288-296, Feb. 2006.

R. A. Jones, et al., k-Space Substitution: A Novel Dynamic Imaging Technique, Magn. Reson. Med. 29(6): 830-834, Jun. 1993.

Prodromos Parasoglou, Optimal k-Space Sampling for Single Point Imaging of Transient Systems, J. Magn. Reson. 194(1): 99-107, Sep. 2008.

P. Parasoglou, et al., Quantitative Single Point Imaging with Compressed Sensing, J. Magn. Reson. 201(1): 72-80, Nov. 2009.

A. K. Nandi, Quality of Signals Reconstructed from Degraded Fourier Transform Phase, Electronic Letter 26(18): 1460-1462, Aug. 1990.

Stephane G. Mallat, Multiresolution Approximations and Wavelet Orthonormal Bases of L2(R), Trans. Amer. Math. Society 315(1): 69-87, Sep. 1989.

Konstantin Romanenko, Bruce J. Balcom, Permeability Mapping in Naturally Heterogeneous Sandstone Cores by Magnetization Prepared Centric-Scan SPRITE, AIChE Journal 58(12): 3916-3926, Dec. 2012.

Angshul Majumdar, Rabab K. Ward, Accelerating Multi-Echo T2 Weighted MR Imaging: Analysis Prior Group-Sparse Optimization, J. Magn. Reson. 210(1): 90-97, May 2011.

H. Y. Carr, E. M. Purcell, Effects of Diffusion on Free Precession in Nuclear Magnetic Resonance Experiments, Phys. Rev. 94(3): 630-638, May 1954.

J. Mitchell, et al., Obtaining True Transverse Relaxation Time Distributions in High-Field NMR Measurements of Saturated Porous Media: Removing the Influence of Internal Gradients, J. Chem. Phys. 132(24): 244705, Jun. 2010.

Dan Xiao, Bruce J. Balcom, Two-dimensional T2 Distribution Mapping in Rock Core Plugs with Optimal k-Space Sampling, J. Magn. Reson. 220: 70-78, Jul. 2012.

K. Romanenko, et al., Velocity Field Measurements in Sedimentary Rock Cores by Magnetization Prepared 3D SPRITE, J. Magn. Reson, 223: 120-128, Oct. 2012.

Dahai Chang, et al., Effective, Producible Fluid, and Permeability in Carbonates from NMR Logging, paper in SPWLA 35th Annual Logging Symposium, Jun. 19-22, 1994.

\* cited by examiner

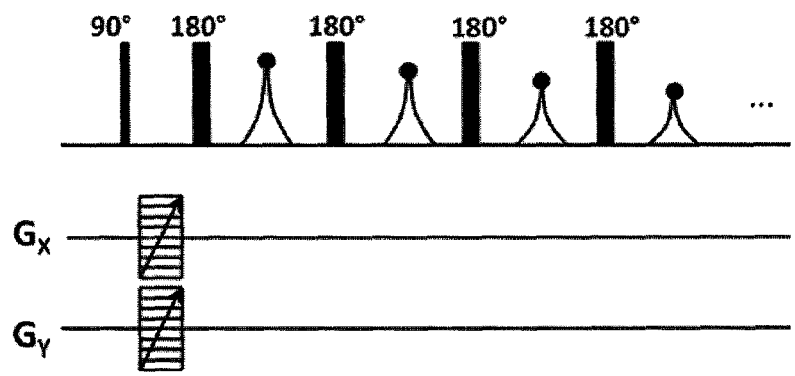
FIG. 1
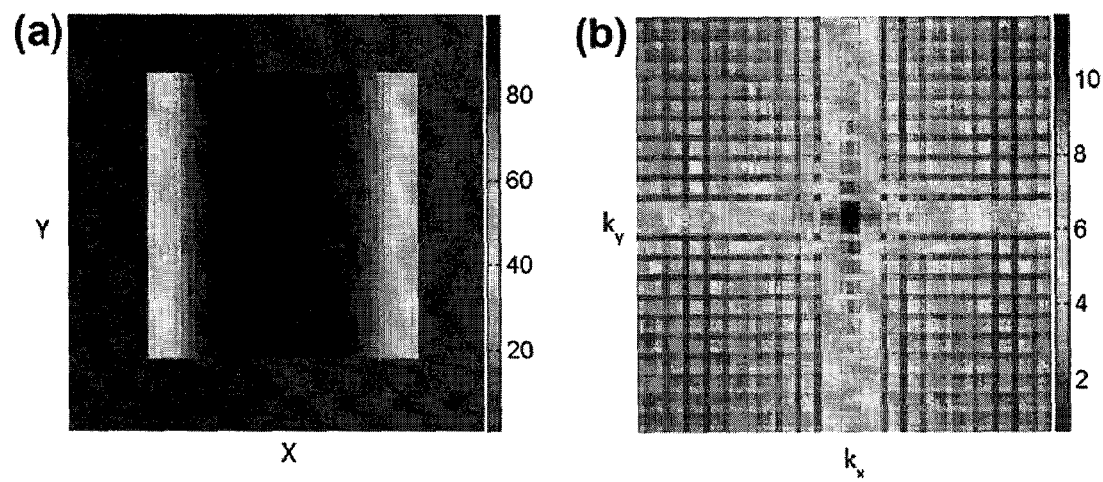
FIGS 2(a) and (b)

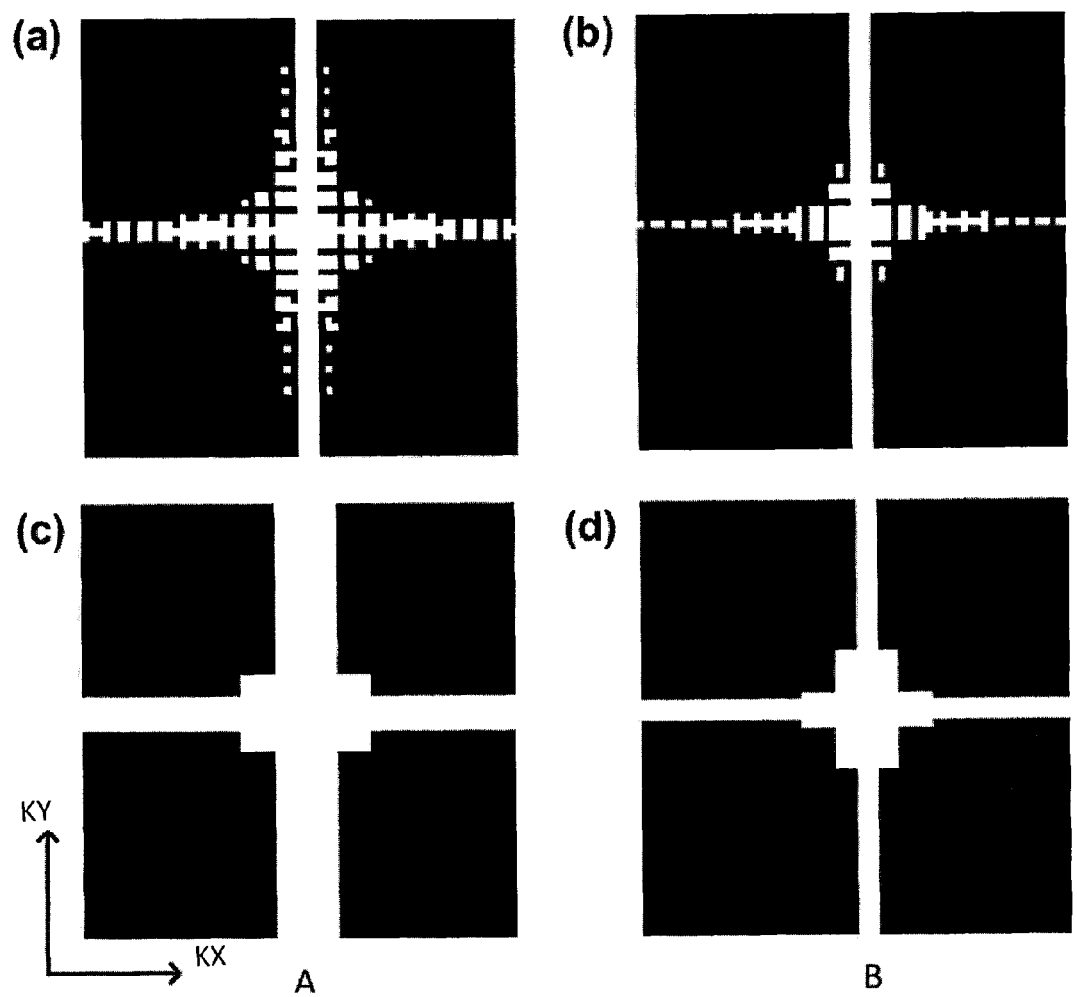
FIGS 3(a)-(d)

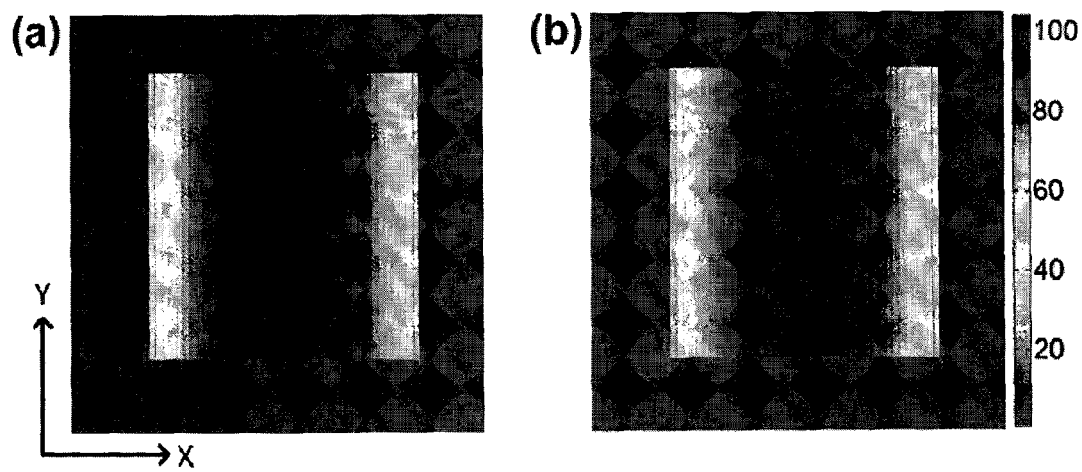
FIGS 4(a) and (b)

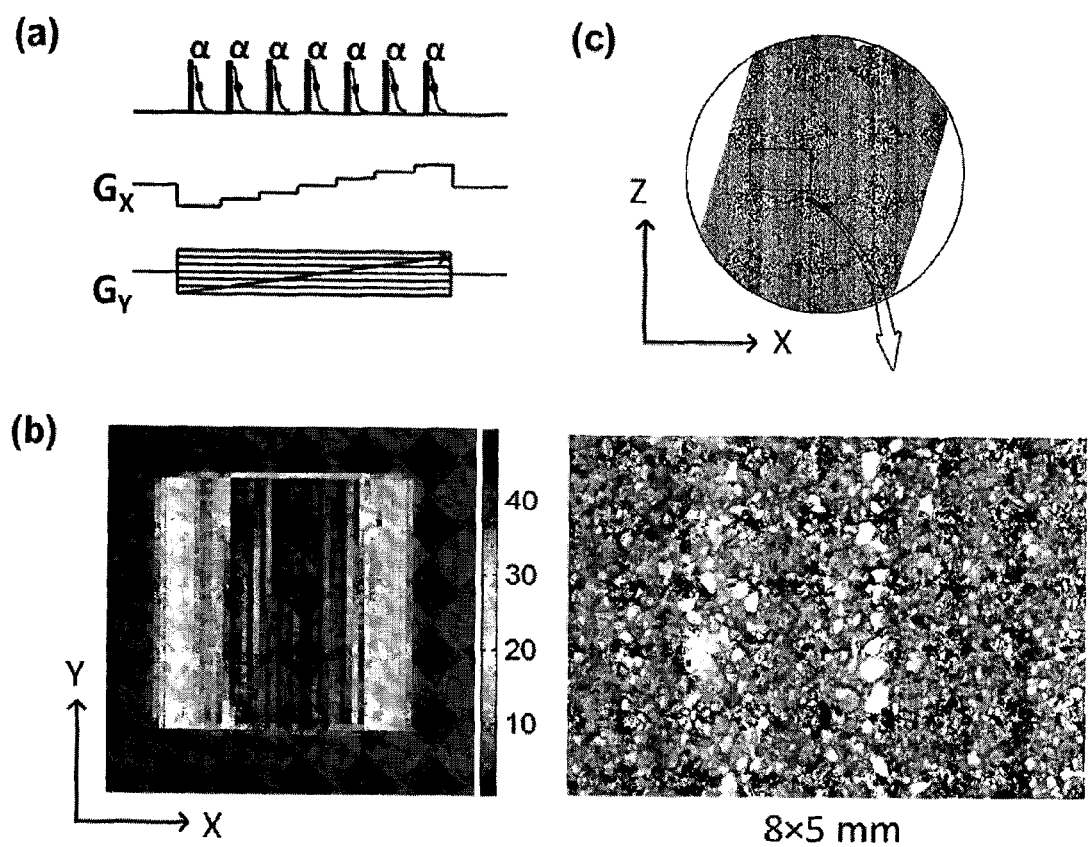
FIGS 5(a)-(c)

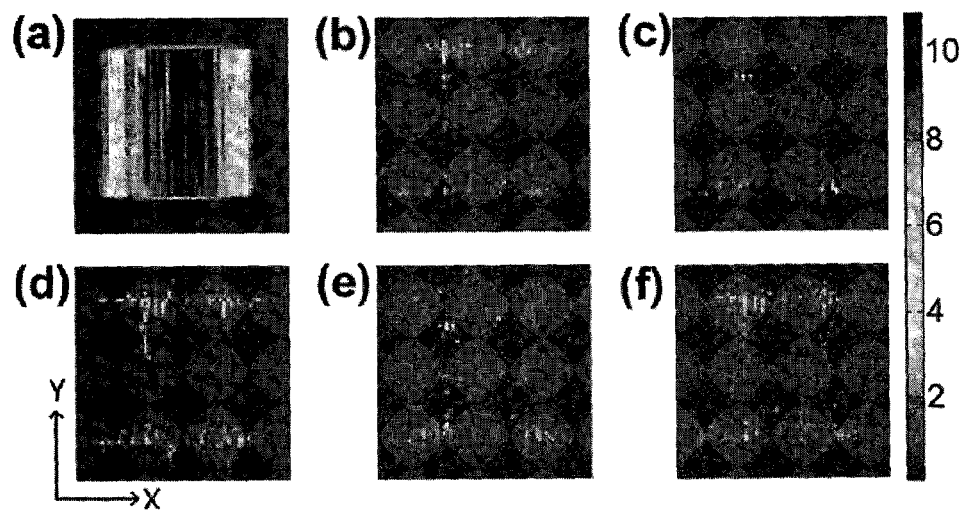
FIGS 8(a)-(f)
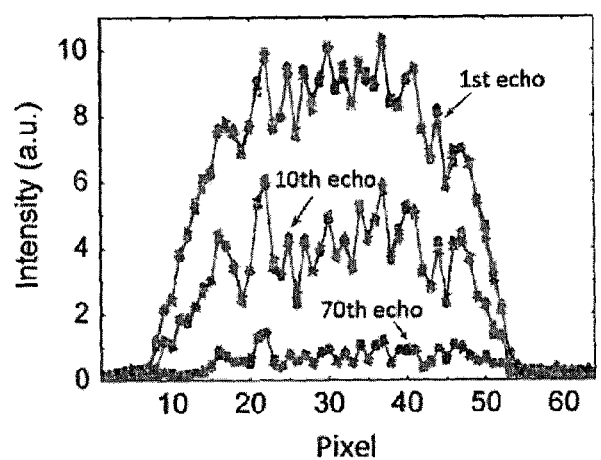
FIG. 9

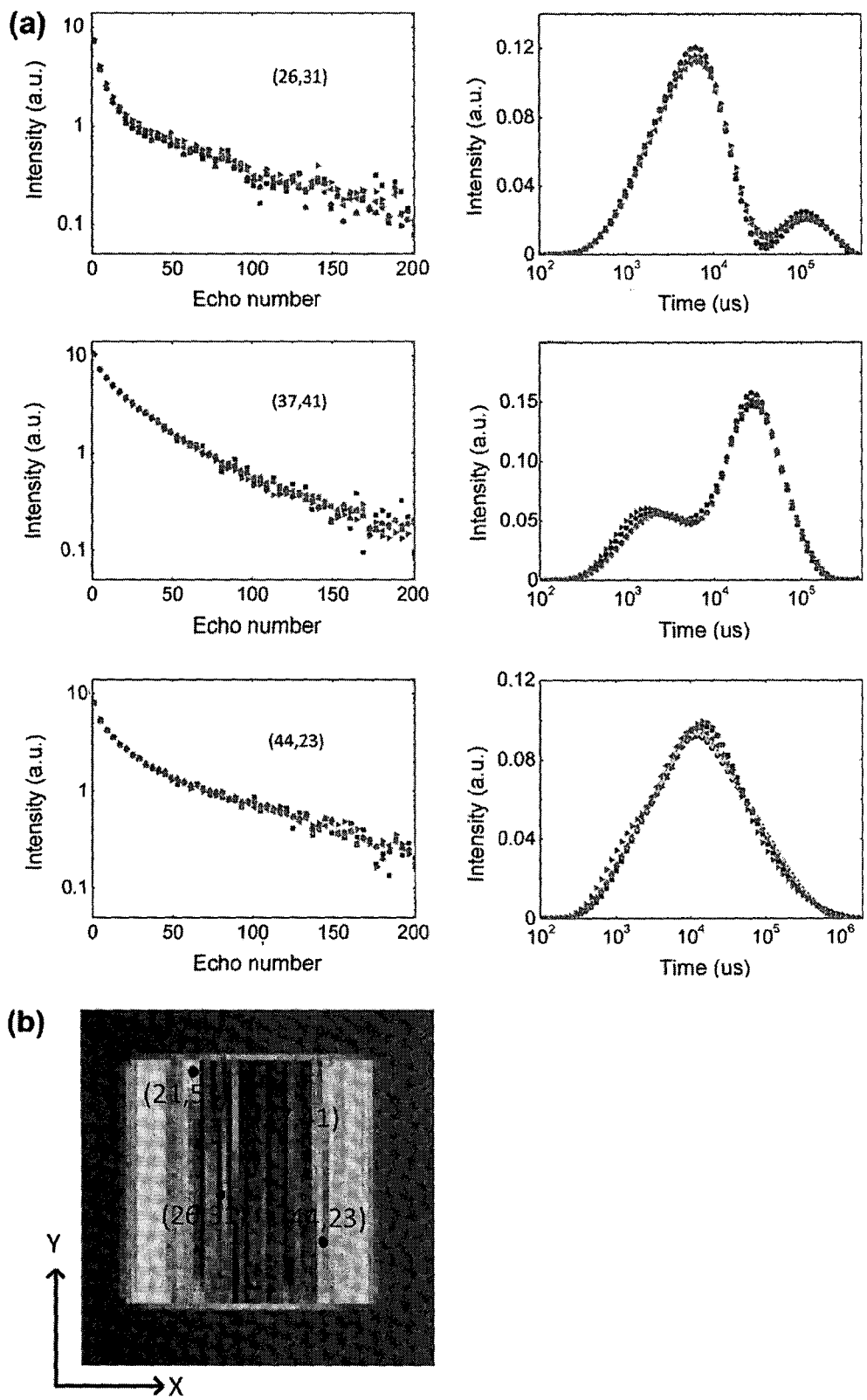
FIG. 11(a) and (b)

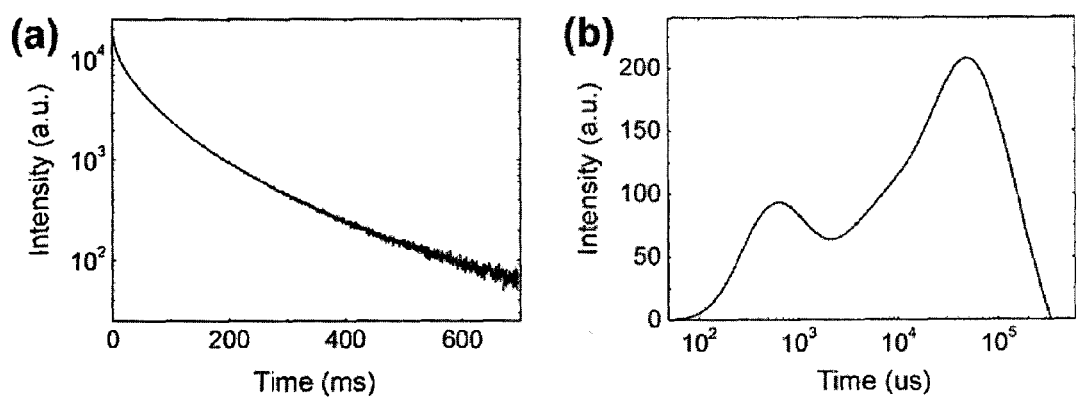
FIGS 12(a) and (b)
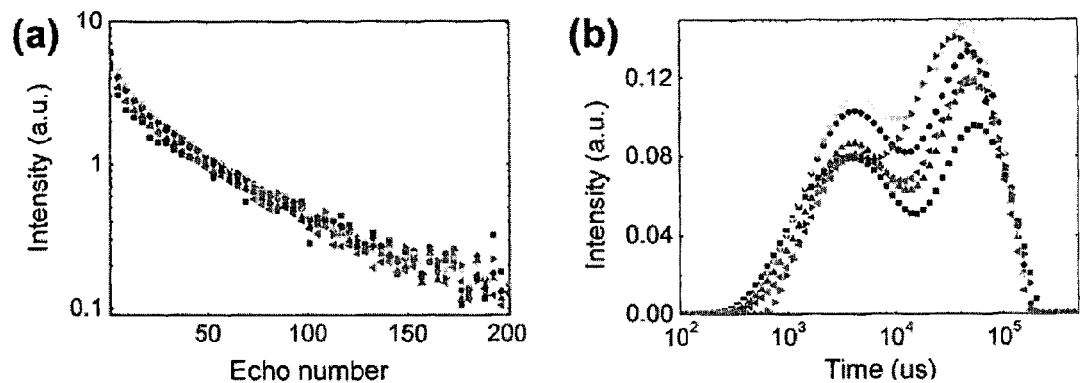
FIGS 13(a) and (b)

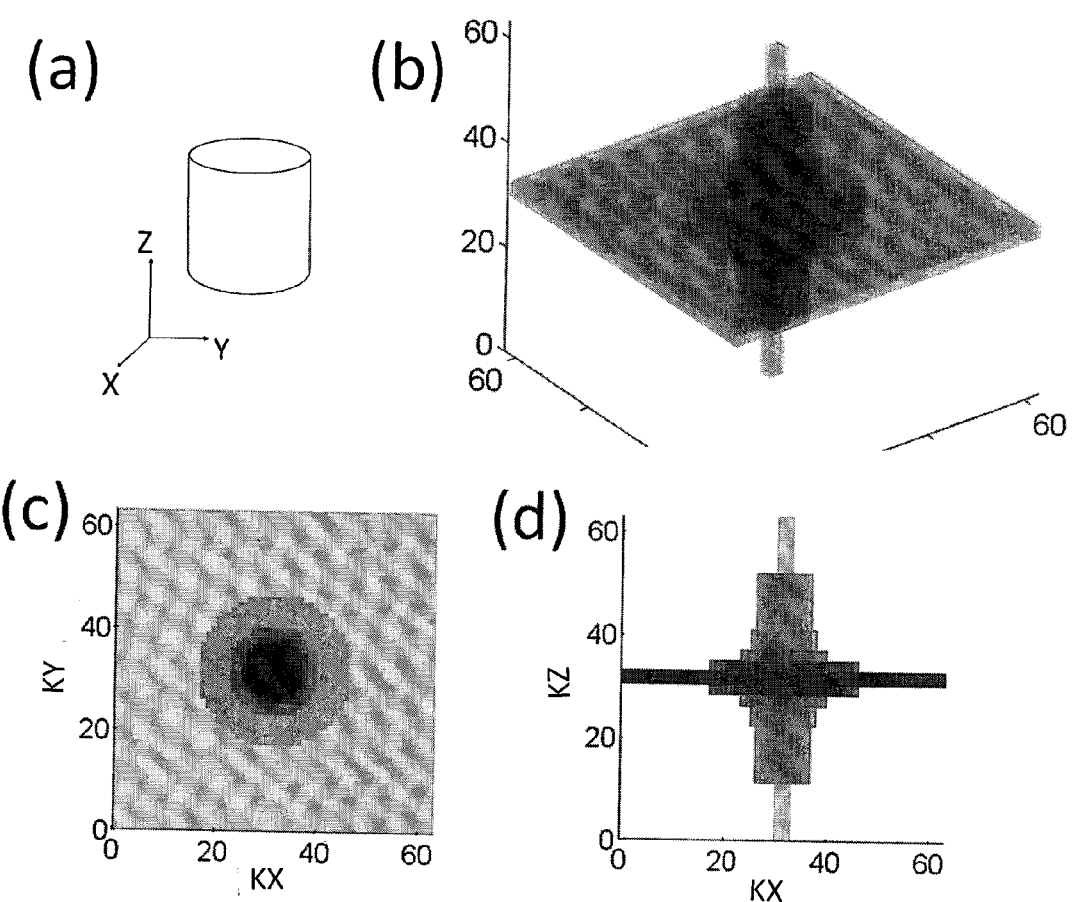
FIGS 14(a)-(d)

US 9,702,953 B1

METHOD OF SAMPLING IN PURE PHASE ENCODE MAGNETIC RESONANCE IMAGING

CROSS-REFERENCE TO RELATED APPLICATIONS

None.

FIELD

The present invention relates to magnetic resonance imaging ("MRI").

BACKGROUND

NMR relaxation time distribution measurements in porous media are commonly undertaken to determine the pore size distribution and play an important role in the characterisation of porous media including permeability, wettability, capillary pressure, residual oil saturation and gas volume [1-3]. The $T_2$ relaxation time distribution measurement is the essential basis of most downhole NMR logging measurements [4-10]. The $T_2$ distribution measurement in this case is a bulk measurement from a region of space defined by the magnet and RF probe geometry.

Relaxation time distribution studies in the literature are almost entirely bulk measurements despite the fact that reservoir rocks, and reservoir core plugs, are frequently macroscopically heterogeneous. $T_2$ relaxation time distribution mapping is highly desirable because the bedding plane structure, ubiquitous in sedimentary rocks, and frequently finer scale than the core plug itself, will often result in different pore properties within the sample.

Commonly employed multi-echo $T_2$ mapping sequences with frequency encode gradients are not suitable for this purpose because of the inherently short relaxation times [11, 12] and strong susceptibility contrast [13] in reservoir rocks. Pure phase encode techniques are robust in their ability to generate true fluid content images and relaxation mappings in porous media [14-17]. Li measured 1D spatially resolved $T_2$ distributions with separate phase encoding of each echo in a multi-echo CPMG pulse train [15]. This method is not optimal in terms of gradient duty cycle and gradient stabilization, as phase encoding and phase unwinding gradients are required for each echo. Petrov et al [16] improved the Spin Echo Single Point Imaging (SE SPI) method by restricting phase encoding to the first pulse interval preceding readout through multiple refocusing. A CPMG prepared SPRITE (Single Point Ramped Imaging with $T_1$ Enhancement) sequence for $T_2$ distribution mapping has also been proposed [17].

The SE SPI experiment has great utility for routine rock core plug measurements, but has an acquisition time that is proportional to the number of k-space points. This makes simple Cartesian sampling unrealistic for the 2D case. Petrov et al employed Compressing Sensing (CS) [17] to mitigate the problem. In the current work, optimal k-space sampling schemes are developed to improve the measurement time.

Undersampling k-space has been a popular topic in MRI research for decades [18-20]. Compressed sensing reconstruction has been successfully applied to MRI [21] and may achieve high acceleration factors. However, the calculations can be time consuming and CS sometimes yields unreliable results, especially for low contrast features.

Geometric k-space sampling patterns are very natural and are routinely employed in centric scan SPRITE [22, 23]. Sampling patterns which utilize radial, spiral, conical or sectoral trajectories omit the extremes of k-space in a Cartesian representation. These omitted points are assigned a value of zero. This approach is simple and reliable but saves only 20% of the k-space data points in 2D, resulting in minor reductions in acquisition time.

Spin-echo single point imaging has been employed for one dimensional ("1D") $T_2$ distribution mapping, but a simple extension to two-dimensional ("2D") is challenging since the time increase is n fold, where n is the number of pixels in the second dimension. Nevertheless 2D $T_2$ mapping in fluid saturated rock core plugs is highly desirable because the bedding plane structure in rocks often results in different pore properties within the sample.

SUMMARY OF THE DISCLOSURE

In one implementation, the present disclosure is directed a method of magnetic resonance imaging of a sample including sampling in pure phase encode MRI including restricting sampled points to a specified region.

In another implementation, the present disclosure is directed to imaging rock core plugs with multidimensional MRI, where the samples are of a regular cylindrical shape that yields well defined intensity distributions in reciprocal space. A large portion of the k-space points have very low intensities that are below the noise level. These points can be zero-filled instead of being collected experimentally. In certain other implementations, the present disclosure is directed to applying the k-space sampling patterns in pure phase encoding measurements, such as $T_2$ mapping SESPI [34], single echo SESPI, hybrid-SESPI [15] and SPRITE [22], since all imaging dimensions can be under-sampled. Since fewer points need to be collected, fewer experimental data points the image acquisition is faster.

In another implementation, the present disclosure is directed to a method of sampling in pure phase encode magnetic resonance imaging which includes undersampling k-space whereby acquisition time is improved. When a cylindrical shaped rock core plug is the object being imaged, the cylindrical shape of rock core plug yields well defined intensity distributions in k-space that may be determined by k-space sampling patterns according to implementations of the present disclosure. In an implementation of the present disclosure, these patterns acquire 22.2% and 11.7% of the k-space data points. With the remaining points set to zero, these sampling patterns, upon Fourier transformation, yield good quality images. In other implementations of the present disclosure, companion density images may be employed, in a keyhole imaging sense, to improve image quality. $T_2$ weighted images are fit to extract $T_2$ distributions, pixel by pixel, employing an inverse Laplace transform. In other implementations of the present disclosure, images are reconstructed with compressed sensing, with similar acceleration factors.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 1 shows a prior art 2D Spin-echo Single Point Imaging sequence. The magnetization is phase encoded during the first pulse interval and then read out through multiple refocusing. Composite 180° pulses ($90_0 180_{\pi/2} 90_0$) were employed for RF field inhomogeneity compensation. 64 gradient steps were employed for each dimension;

FIGS. 2(a) and (b) show a model of a uniform core plug sample and its k-space representation. In FIG. 2(a), the sample occupies 43 pixels vertically and 42 pixels horizontally in a 64×64 image, approximately ⅔ of the FOV in both dimensions. In FIG. 2(b), k-space magnitude plotted as ln(|Signal|+1). The high intensity points are concentrated along the horizontal and vertical axes;

FIGS. 3(a)-(d) show k-space sampling masks. Sampled points determined by intensity thresholds 0.2% in FIG. 3(a), and 0.4% in FIG. 3(b). Modified patterns are shown in FIG. 3(c) with 911 points, and in FIG. 3(d) with 479 points. Patterns A and B correspond to FIGS. 3(c) and 3(d) above respectively, and each includes intermediate points of the threshold patterns;

FIGS. 4(a) and (b) show simulated images of a uniform cylinder reconstructed with the proposed sampling patterns with unsampled points zero-filled. Images reconstructed with patterns A, and B from FIG. 3 are presented in FIG. 4(a) and FIG. 4(b) respectively. The correlation to the original image, FIG. 2(a), is high, with only slight blurring effects near the corners. Pattern A performs better as expected;

FIGS. 5(a)-(c) show a standard SPRITE sequence and images of the Corncockle core plug sample. FIG. 5(a) shows the SPRITE pulse sequence. 64 steps were used in each dimension. FIG. 5(b) shows XY 2D SPRITE image of the Corncockle Sample. The cylindrical axis of the sample lies in the y-direction. This data was employed as the template for SE SPI experiments after phase and amplitude corrections. The planar structure within the sample is readily apparent. FIG. 5(c) is an optical photograph of a 30 μm thin section from the end of the sample (XZ plane), including an expanded view shown in gray to emphasize the grain size variation. The circular thin section was trimmed for an SEM experiment. The optical image is rotated so as to correspond to the plane orientation in FIG. 5(b). The bedding planes are distinguished by variations in color and grain size. Note that the structure in the photograph is very similar to that in the SPRITE image;

FIGS. 8(a) to (f) show differences of reconstructed images from the 1st echo in the SE SPI measurements. FIG. 8(a) is a reference image and corresponding difference images from FIG. 8(b) Pattern A with zero-filling, FIG. 8(c) shows A with template, FIG. 8(d) shows B with zero-filling, FIG. 8(e) shows B with template and FIG. 8(f) shows compressed sensing. The intensities have been multiplied by 4 for the difference images to better visualize the results. The differences are all very small. Pattern A combined with template data yields the least differences from the reference image;

FIG. 9 shows 1D slice profiles of the central pixel of core plug long axis from 2D SE SPI images of the 1st, the 10th, and the 70th echoes. Different reconstructions are displayed as ■ reference from full k-space acquired experimentally, ● undersampling pattern A with the remaining points zero-filled, ▲ pattern A combined with the template data, ▽ pattern B with zero-filling, ◀ pattern B with template data, and ▷ compressed sensing. The results are near identical in all cases;

FIG. 11(a) shows $T_2$ decay and $T_2$ distribution curves from the 3 selected pixels. Symbols are: ■ reference from full k-space acquired experimentally, ● undersampling pattern A with the remaining points zero-filled, ▲ pattern A combined with the template data, ▽ pattern B with zero-filling, ◀ pattern B with template data, and ▷ compressed sensing;

FIG. 11(b) shows pixel positions. Different schemes yield virtually identical results. The $T_2$ distributions vary with position in the sample;

FIGS. 12(a) and (b) show bulk $T_2$ results. FIG. 12(a) shows Decay curve. FIG. 12(b) shows Distribution curve. Short relaxation time components absent from the spatially resolved distributions are present in the bulk measurement because of the shorter echo time;

FIG. 13 shows $T_2$ decay and distribution curves of pixel (21, 53), whose position is indicated in FIG. 11(b). This pixel has the highest level of image reconstruction error. The four undersampling schemes yield similar $T_2$ distribution curves with identical peak positions. The intensities are higher than that of the reference, but can be easily corrected with a fluid density image. The result from compressed sensing is erroneous because the reconstruction is insensitive to low contrast features. Symbols are: ■ reference using a full k-space acquisition, ● undersampling pattern A with the remaining points zero-filled, ▲ pattern A combined with the template data, ▽ pattern B with zero-filling, ◀ pattern B with template data, and ▷ compressed sensing;

FIGS. 14(a)-(d) show a three dimensional ("3D") restricted sampling pattern of a sample imaged using a method according to an embodiment of the present invention; and, FIG. 15 schematically shows an MRI measuring system which is suited for carrying out methods according to embodiments of the present invention.

DETAILED DESCRIPTION

Spin-Echo SPI

Figure 6:
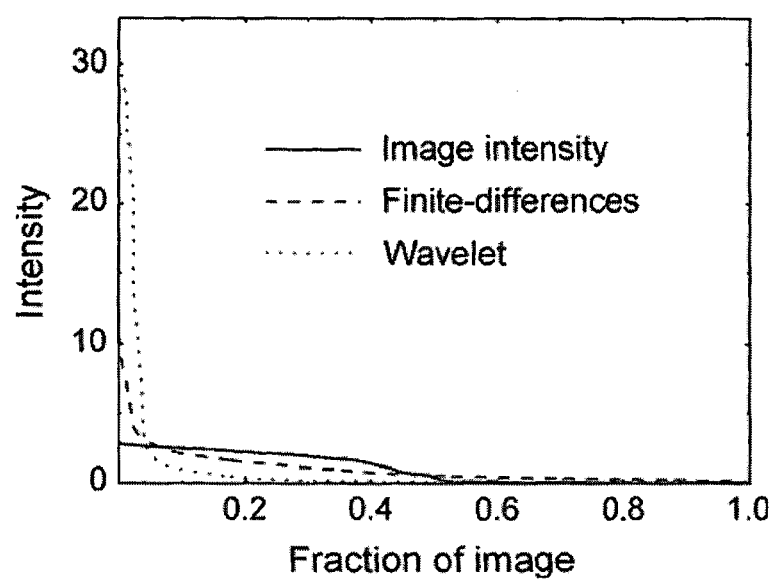
FIG. 6 shows the rank ordered intensity of the first echo SE SPI image in the image, finite-differences and wavelet transform domains. Wavelet is a good sparse representation of the image.

FIG. 1 shows the 2D Spin Echo SPI sequence. It is employed for spatially-resolved $T_2$ distribution measurements, termed $T_2$ mapping. In the sequence, spatial encoding with phase encode gradients is applied immediately following the 90° pulse and maintained for every echo in the train of spin echoes. One can reconstruct an image from each echo, and each image will have a corresponding $T_2$ weighting. Decay curves for each pixel can be extracted, and the local $T_2$ distribution is determined with an inverse Laplace transform. Note that the lower limit of the first echo time is determined by the gradient amplitude and switching time. Subsequent echo times may be shorter, allowing a higher concentration of echoes for calculations of $T_2$ distributions. Since the first echo time is relatively long, very short $T_2$ components, such as those found in gas shales, will be lost.

SE SPI can be a very time consuming experiment as a relaxation delay of 5×$T_1$ is required between each gradient step. However, since k-space is covered point by point, there is no restriction on trajectories. In the method according to an embodiment of the present invention, the sampling scheme is optimized to reduce the overall acquisition time.

Optimal k-Space Sampling and Keyhole

The low frequency central portion of k-space determines the overall image intensity and structure, while the high frequency periphery contains information on the image fine detail. In general, the signal magnitude decreases as k increases. At the extremes of k-space the signal level is typically comparable to that of the noise, so that frequently these points are zero-filled instead of being collected experimentally. This is an integral feature of radial, spiral, sectoral and conical trajectories in 2D and 3D SPRITE [22, 23], in which k-space points outside a circle or sphere of radius equal to half the matrix size are zero-filled. This strategy generally works well for any sample shape, and introduces an acceptable level of image blurring. The experimental time is reduced and the Signal-to-Noise (SNR) ratio is improved, since less noise is collected when the periphery of k-space is simply set to zero.

Prior knowledge of the sample shape enables the design of more efficient sampling patterns. Since the energy distribution in k-space is better known, one can sample only the high intensity points or regions and set the unsampled parts to zero. Parasoglou et al [25] applied this approach to pure phase encoding measurements since all imaging dimensions can be under-sampled with no constraints on the k-space sampling trajectory.

In some applications, such as the monitoring of a dynamic system, a series of images with different intensities are required. As the fine structure does not change dramatically, the high frequency parts of k-space are essentially similar within the image series. Rather than zero filling, one can acquire a full k-space sampled image and use it as a template for the unsampled points in the other images [24, 25]. This approach, well known in clinical MRI, is termed keyhole imaging.

In one embodiment, the method according to present invention applies keyhole imaging to SE SPI where images are weighted by different $T_2$ attenuations. However, since there are negligible time savings in acquiring the full k-space data for only one echo, a separate experiment can be performed for a high quality density image for use as a k-space template. In another embodiment, the method according to the present invention uses a pure phase encode SPRITE experiment as the source of the template data.

Compressed Sensing

Compressed sensing ("CS") has been successfully applied to MRI by numerous investigators [21, 26]. In this approach, initial images are generated by Fourier transformation of the known data multiplied by a density compensation function. This compensation function is the inverse of the probability density, i.e., points from the under-sampled areas are given higher weights. This is to preserve resolution by increasing the nominal noise that results from incoherent aliasing artifacts. CS reconstruction suppresses these artifacts by finding the sparsest solution in a certain image representation that is also consistent with the known sampled data. It is achieved by solving Eq. [1]:

$$\min_m [([(\|\mathcal{F}_u m - \gamma\|_2)]^2 + \lambda \|\psi m\|_1)] \quad [1]$$

where $\gamma$ are the known points in k-space, m is the desired image, $\mathcal{F}_u$ is a partial Fourier transform, $\psi$ is employed to transform the image to a sparse representation, and $\lambda$ is a regularization factor which quantifies the balance between sparsity and data consistency.

Simulations

Core plugs are universally cylinders. The bedding planes are commonly parallel or perpendicular to the long axis of the core plug. A model core plug sample of uniform intensity is shown in FIG. 2(a). Simple Fourier transformation yields the energy distribution in k-space, shown in FIG. 2(b) plotted as ln(|Signal|+1). The signal is naturally sparse with a large portion of k-space data points close to zero, and the high intensity points largely restricted to the horizontal and vertical axes.

By setting thresholds of 0.2% and 0.4% on the normalised k-space magnitude, two patterns are generated as shown in FIGS. 3(a) and 3(b). The patterns are very sensitive to sample details, such as the sample size to FOV ratio and variation in intensity. Two modified cross shaped patterns including all the intermediate points are generated. FIG. 3(c) is pattern A resulting from a 0.2% threshold with 911 points, and FIG. 3(d) is pattern B with a 0.4% threshold and 479 points, assuming a 64×64 data matrix. These two sampling patterns, with 22.2% and 11.7% of k-space, form the basis of our subsequent discussions of undersampling.

FIG. 4 shows images reconstructed with the proposed sampling patterns A and B, with the unsampled points zero-filled. Pattern A performs better, as we would expect based on the number of points employed. The reconstructed images are both very similar to the original image with only slight blurring effects near the corners. In one embodiment, the method according to the present invention can be used to acquire satisfactory images of a uniform cylinder by sampling 22.2%, or even 11.7%, of k-space.

Realistic samples, of course, are not perfect cylinders with uniform intensity. With non-ideal samples, the performance of these undersampling patterns degrades, since the energy distribution in k-space is not as concentrated in the defined sampling regions. However, the overall intensity and shape are already well defined. Even the detailed structures are to some extent preserved, as the sampling patterns include high frequency components in k-space. The image quality can be further improved by employing a keyhole strategy to acquire the high frequency information, corresponding to the finer image detail. Changes in image intensity can then be monitored efficiently with the sampling patterns in FIG. 3.

A simple and direct keyhole combination can cause various artifacts arising from discontinuities in phase and amplitude between the data sets, requiring corrections to the template data for both phase and amplitude. This includes scaling the template data so that the k-space origin is the same as that of the sampled data, and potential corrections for differing FOV's.

Simulations of the undersampling patterns according to certain embodiments of the present invention on a non-uniform cylindrical sample were performed. Zero-filling the unsampled points yields good results, while employing a homogenous cylinder density image as a template to fill in the remaining points recovers fine detail near the object corners very well (images not shown).

Normalized Mean Square Error ("NMSE") of the signal-containing pixels is employed as a quantitative measure of reconstruction quality [27]. NMSE is defined in Eq. [2], $$E = \frac{\sum_n |I_n - I_{Refn}|^2}{\sum_n |I_{Refn}|^2}, \quad [2]$$

where $I_n$ and $I_{Ref_n}$ are the signal intensities of the nth pixel of the reconstructed image and reference image, respectively. Noise pixels are not included in the calculation. The simulated reconstructed images of a non-uniform cylindrical sample, with sampling pattern A, sampling pattern B, with zero-filling and with the template, have NMSEs of 0.006%, 0.026%, 0, 0, respectively. The errors of simply zero-filling cases are very low, while combining template data yields zero error indicating the reconstructed images are the same as the reference.

Spin Echo SPI Experiment

Full k-space data sets were collected in the SE SPI experiment to make comparisons between different reconstruction schemes. The total acquisition time was 4.3 hours for a full 2D 64×64 k-space data set.

The core plug sample was a Corncockle sandstone with a planar structure saturated with distilled water. The sample was oriented so that the bedding planes were parallel to the YZ plane. MRI images were acquired in the XY direction, side on. A high quality density image from a standard SPRITE [14] experiment was employed as a template. The SPRITE pulse sequence is shown in FIG. 5(a). In SPRITE, the phase encoding gradients are ramped in discrete steps so that k-space was sampled in a linear raster commencing at the extremities of k-space. The standard SPRITE trajectory was chosen over a centric scan trajectory [22] because all k-space data were required. A centric scan also yields a higher intensity at the k-space origin which could cause additional problems in amplitude correction. FIG. 5(b) shows the density image. The planar structure within the sample is readily apparent indicating basic differences in the underlying pore microstructure. No bedding planes are apparent by eye in the core plug sample. However, this structure is readily apparent in a high resolution, back lit, optical image of a 30 μm thin section taken in the XZ plane from the end of the sample, FIG. 5(c). The reddish hue, differing between bands, helps define the planes. The expanded portion reveals different grain sizes as well. Note that the bedding plane structure in the photograph is very similar to that in the SPRITE image, FIG. 5 (b).

For CS reconstruction, it is crucial to choose a proper sparsifying domain. A simple measure of sparsity is the percentage of transform coefficients that cover sufficient energy for a good quality reconstruction. A good sparse domain has signals concentrated in a small number of voxels. The rank ordered intensity of the first echo SE SPI image in the image, finite-differences and wavelet transform domains are shown in FIG. 6. To cover 80% of the total energy, it requires 35.2%, 43.1% and 6.3% of the total coefficients for image, finite-differences and wavelet transforms, respectively.

It is clear that wavelet is a good sparsifying domain, while finite-differences is not, a result of the sample not being piecewise constant. If finite-differences were chosen as the sparsifying transform, fine detailed structures, particularly low-contrast features, would be smoothed out. In the method according to an embodiment of the present invention, a wavelet transform [28] is employed as the sparse transform to preserve fine detail. The wavelet transform is a multi-resolution representation of the image. Fine-scale coefficients representing high resolution components are usually sparse, while coarse-scale coefficients representing low resolution components are not. This results in good performance of the high frequency parts, and reduced performance at lower frequencies after $l_1$ norm reconstruction. Care must be taken not to under-sample too much the low frequency regions.

The sparse sampling scheme is also essential in CS. The artifacts resulting from undersampling need to be incoherent so that they can be eliminated by the CS reconstruction. The incoherence can be measured by the maximum of the sidelobe-to-peak ratio ("SPR") of the Transform Point Spread Function ("TPSF") in the sparse domain [21]. The initial image after partial Fourier transformation is also important in the CS reconstruction, especially when the sparsity is not optimal. CS can only remove noise-like incoherent aliasing artifacts, i. e., it tends to highlight high-contrast features and smooth out low-contrast noise-like features. CS can not recover the low-contrast features that are missing in the initial image, so it is important that the initial image reveals all important structures.

In one embodiment, in the method according to the present invention, the same undersampling pattern as proposed in the keyhole pattern B is kept, plus additional random points outside of this area to increase the k-space sampling factor to 20%. The Daubechies wavelet [29] was employed as the basis.

This sparse sampling scheme produces very low peak interference in coarse and medium scale wavelet coefficients. Low peak interference is also manifest in the corner of fine-scale coefficients that represents high frequency in both directions. Though the vertical and horizontal high frequency coefficients constitute higher peak interference than the commonly used 2D variable density random undersampling scheme, this particular sparse sampling scheme was chosen over the latter because it covers most high energy k-space points. The sparse scheme employed covers sufficient energy since even the linear reconstruction with pattern B and the remaining k-space points zero-filled yields good quality images. On the contrary, variable density random undersampling of even 50% of k-space yields poorer results. Due to the special sample structure and sparsity in the transformed domain, CS can not recover detailed structures if they are not revealed in the initial image. The sparse scheme employed can be considered nearly optimal in this particular case.

Figure 7:
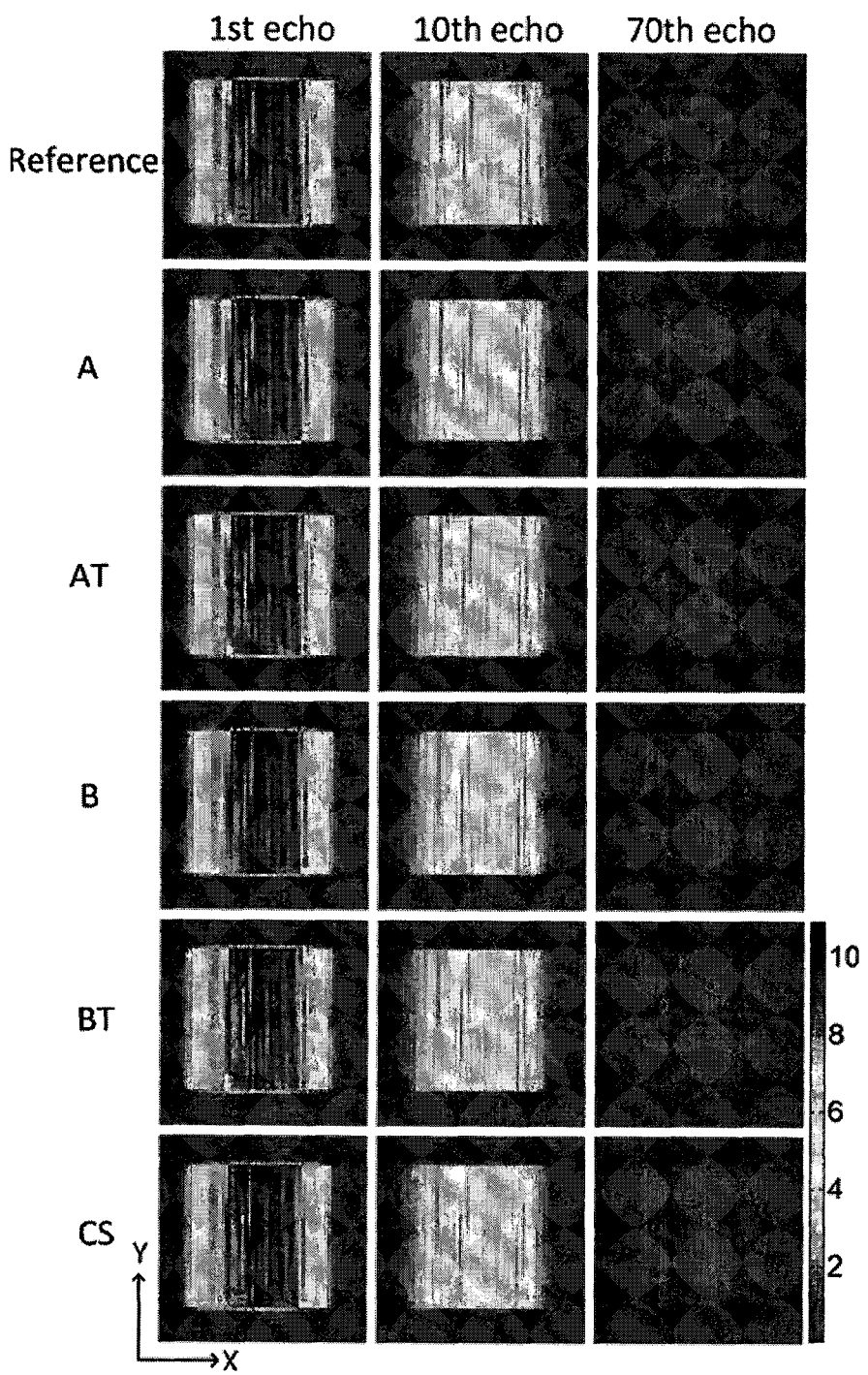
FIG. 7 shows SE SPI results. Full k-space reference images from the 1st, 10th, and 70th echoes, and reconstructed images, along with sampling Pattern A with zero-filling (labeled as A), A with template (AT), B with zero-filling (B), B with template (BT), and compressed sensing (CS). Key features are reproduced in all images. The reference images have a lower SNR, particularly in the later echo images.

Reference images from the SE SPI measurement together with images reconstructed with different schemes from the 1st, 10th, 70th echoes are shown in FIG. 7. The reference images very closely resemble the SPRITE density image in FIG. 5(b), confirming that the intensity differences are due to sample features rather than imaging artifacts. The similarities also substantiate the validity of the keyhole approach. For the 1st echo images, some detailed structures in the reference image are not present in the zero-filled reconstructions. In these cases, noise level data were replaced by zeroes, so the reconstructed images appear to have a higher SNR. The images combining SPRITE data in a keyhole fashion, carrying the high frequency information of the density image, recover fine details very well, although the noise level is slightly higher. The CS image has a higher SNR because it is inherently a denoising procedure. Difference images from the 1st echo are displayed in FIG. 8. Pattern A, with template data, yields the closest image to the reference. CS reconstruction, on the other hand, yields a similar result to pattern B with zero-filling.

Overall image intensity decreases as the echo number increases due to $T_2$ attenuation. Medium and low intensity echo images are also shown in FIG. 7. Scaling of the template data resulted in the noise level being lowered for the high frequency components as the overall intensity decreases, improving the SNR. Cases employing the template are of a higher SNR than the reference images. CS reconstruction is less robust when the SNR is low, which yields the largest difference from the reference (not shown).

For a better perspective of the reconstructed images, 1D slice profiles through the central pixel of the core plug long axis from 2D SE SPI images are shown in FIG. 9. The profiles from different schemes are largely identical so that the data symbols for the 1st, 10th and 70th echo images overlap. Good quality reconstructed images, of each echo, are a prerequisite for accurate $T_2$ distribution mapping.

Figure 10:
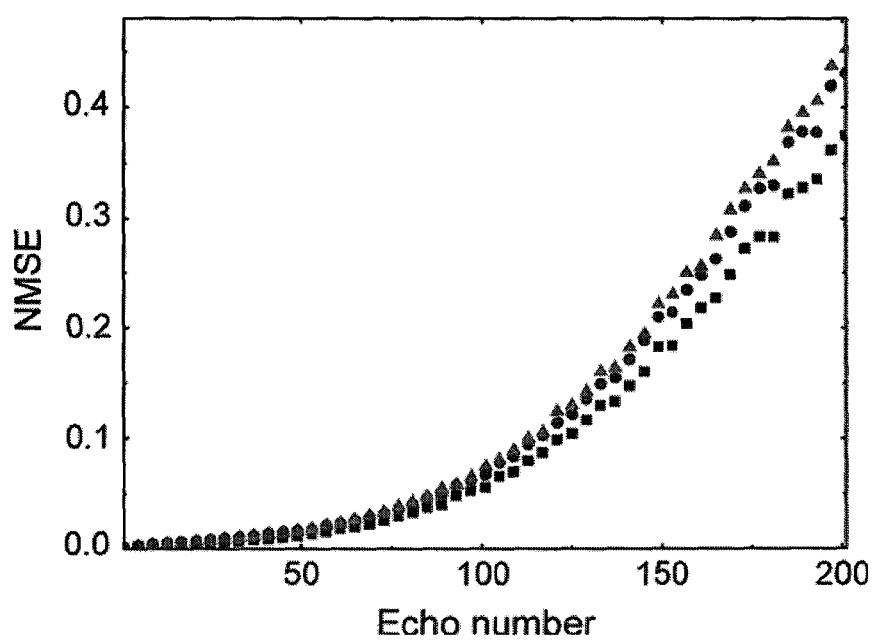
FIG. 10 shows normalized Mean Squre Errors (NMSE) of ■ pattern A and ● pattern B with the unsampled points zero-filled, and ▲ compressed sensing. The NMSEs of reconstructions with template data are almost identical to the corresponding zero-filling scenario, not shown.

NMSEs for different schemes were calculated as a quantitative measure of reconstruction quality in FIG. 10. The errors for the two undersampling patterns with templates (not shown) are almost identical to the corresponding zero-filled cases. Those reconstructed with more k-space points have lower errors, as expected. CS yields the highest error, but still less than 5% up until the 85th echo. Error grows fast for later echoes as the SNR decreases. The full k-space data set has the lowest SNR, as explained above. Using it as the reference to calculate normalized errors is not appropriate for low intensity images, as it leads to large errors for later echoes. NMSE is not the best measure in the $T_2$ mapping sense as it estimates the overall error of the whole image. The quality of the local $T_2$ decay data and the resulting $T_2$ distribution are how we best judge the results.

The $T_2$ decay curves of three chosen pixels, extracted from images with different undersampling and reconstruction schemes, are very similar, as can be seen in FIG. 11(a). The $T_2$ distribution curves are also very similar. Different sampling patterns and reconstruction methods yield near identical results. The $T_2$ distribution of pixel (37, 41) has two peaks at about 2 ms and 30 ms with a 30% weighting of the short component, while pixel (44, 23) is centered around one peak at about 15 ms. The third pixel (26, 31) has a 90% weighting of the short component at 6 ms, but also reveals a long $T_2$ contribution at about 110 ms. The $T_2$ distributions are remarkably similar within particular bedding planes (not shown), while substantially different between planes. This confirms the different nature of the pore microstructure in different bedding planes.

The variation of the $T_2$ distributions between bedding planes has not been previously reported. It is consistent, however, with the $T_2^*$ variation from a different experiment methodology [30]. $T_2^*$ and $T_2$ relaxation contrasts are both related to the microstructure of different bedding planes. The SPRITE image in FIG. 5(b) reveals a $T_2^*$ contrast in the bedding planes, while the SE SPI echo images show $T_2$ contrast, both of which are consistent with the bedding plane structure. This validates the use of the SPRITE image in the reconstruction of under-sampled SE SPI data, revealing the microstructural variations in a core plug.

Imaging results obtained in this example are consistent with the optical photo in FIG. 5(c). Variations in mineral content and, by extension, magnetic susceptibility, are indicated by the different colored bands. Different grain sizes between bands are also observed upon magnification. The dependence of $T_2$ and $T_2^*$ on magnetic susceptibility, surface relaxation and pore size is reflected in the patterns observed in the SPRITE and SE SPI images.

The bulk $T_2$ decay and bulk $T_2$ distribution are shown in FIG. 12. The bulk $T_2$ distribution is similar to those in FIG. 11, but not identical, as it is the summation over all the pixels. There are two peaks on the bulk distribution curve at 0.6 ms (20%) and 50 ms (80%). The short $T_2$ components, less than a millisecond, are mostly absent in the SE SPI $T_2$ maps due to the long first echo TE, which is limited by the gradient switching speed.

On a pixel-by-pixel basis, the different acquisition schemes yield very similar results. Reconstruction inaccuracies are greater in pixels near the circular faces of the sample. This can be seen in the error images in FIG. 8. The pixel (21, 53), whose position is indicated in FIG. 11(b), has the highest reconstruction error due to the low contrast fine features. Its $T_2$ decay and distribution curves are shown in FIG. 13. The four undersampling schemes yield similarly shaped distribution curves with identical peak positions at 4 ms (50%) and 50 ms (50%). The intensities of the $T_2$ distribution peaks are higher than the reference, but can be easily corrected with a density image, exploiting the fact that the area under the distribution curve represents the fluid density.

The distribution calculated from the CS reconstructed images is notably different. One of the $T_2$ distribution peaks has similar intensity to the corresponding reference peak, while the other is much higher than the reference. The weighting of the short component here is only 30%. The CS reconstruction is insensitive to low contrast features and vulnerable to low SNR. It does not guarantee consistency between echoes, since the correlation between images derived from each echo was not taken into account [31]. On the other hand, the simple keyhole undersampling patterns are consistent in terms of error between images from each echo of the SE SPI experiment. If, for example, a particular pixel with special structure can not be reconstructed 100% accurately, the same effect occurs for all the echoes and the overall distribution curve retains the correct shape. In this application these strategies are more robust than CS.

It should be noted that the 'cross' sampling patterns A and B of FIGS. 3(c) and 3(d), based on threshold, depend not only on the sample shape, but also the length-to-FOV ratio. The smaller this ratio, the more k-space data points are required, particularly in the zero-filling case. However, the criterion is not strict if the unsampled points are supplemented by a template. The undersampling patterns work well even for zero-filling because the central parts of k-space as well as the most important high frequency components are included.

Compressed Sensing enforces sparsity of a transformed image representation. It's less robust when the SNR is poor and insensitive to low contrast features. In our case, the easy and appropriate sparse domain is actually k-space. Undersampling by exploiting redundancy in k-space yields more reliable results.

$T_2$ measurements of porous media are known to be influenced by molecular diffusion in magnetic field gradients [32] which are more pronounced at high magnetic field due to susceptibility contrast. However, the background gradient can be deconvolved from the CPMG $T_2$ measurement [33]. This methodology can be applied to the SE SPI experiment to ensure that high field measurements are valid and can be post processed to yield the true $T_2$ relaxation distribution.

Experimental

The experiments were performed on a Nalorac (Martinex, Calif.) 2.4T 32 cm i.d. horizontal bore superconducting magnet with a water cooled 7.5 cm Nalorac gradient set (maximum gradient strength 25 G/cm) driven by a Techron (Elkhart, Ind.) 8710 amplifier. The RF probe was a homemade 4.5 cm diameter birdcage probe driven by a 2 kW AMT (Brea, Calif.) 3445 RF amplifier, with a 90°-pulse duration of 11.2 µs. The console was a Tecmag (Houston, Tex.) Apollo. The experiments were performed at ambient magnet temperature, approximately 10° C.

The sample was a 4.0 cm long and 3.8 cm diameter Corncockle sandstone cylinder saturated with distilled water.

The thin section was cut from the end of the sample with a diamond saw and mounted on a glass slide with epoxy resin. The photograph was taken with Canon PowerShot G10 digital camera, back lit with a homemade light box. The photograph was then processed with Photoshop to further correct the white balance to achieve a white background.

In the SE SPI experiment, composite 180°-pulses ($90°_0$-$180°_{\pi/2}$-$90°_0$) were employed. The echo time was 1100 µs for all intervals of 201 echoes (first echo and 200 loops of the CPMG train). The maximum gradient strengths were 7 and 5 G/cm for X and Y directions, respectively. 4 scans were signal averaged with CYCLOPS phase cycling. The total acquisition time was 4.3 hours for a full 64×64 k-space data set.

In the standard SPRITE experiment, 1.5 µs RF pulses were employed for 12° flip angles. The maximum gradient strengths were 14 and 11 G/cm for X and Y directions, respectively. 64 scans with CYCLOPS phase cycling were averaged to achieve a good SNR. Experiment time was approximately 1 hour.

The $l_1$ norm in the CS reconstruction was solved with a nonlinear conjugate gradient method following the approach of Lustig et al [21]. 20 seconds were required to reconstruct each single echo image.

$T_2$ distributions were determined by the WinDXP (Oxford Instruments, Oxford) Laplace inverse transform algorithm in both bulk and spatially resolved cases. The regularization factor was based on noise estimation. The parameter may vary, mostly around the range from 0.8 to 2, between pixels. For each pixel, the parameters were kept the same for different reconstruction schemes to ensure the differences from the full k-space reference image, if any, are not due to the regularization.

When modeling the 2D sample k-space with an ideal cylinder, the high intensity points are concentrated along the horizontal and vertical axes. There are also some low intensity points within the same region. The locations of these points are sensitive to the sample length to FOV ratio, sample detailed structure and the phase of the image. The sample detailed structure and phase are unknown and less predictable which would affect the accuracy of the restricted sampling results. However, the overall region of k-space with high intensity points does not change dramatically as the internal structure of the core plugs changes. In one embodiment of the present invention, restricting the sampled points to the specified region, including the intermediate low intensity points in the k-space model, ensures the coverage of high intensity points in the measurement. This takes about 12% of k-space points for 2D with a threshold of 0.4%, for sample length/FOV=⅔ in both dimensions.

In another embodiment, the method according to the present invention is extended to three dimensional pure phase imaging ("3D Imaging"). In 3D Imaging, the high intensity points are concentrated around the cylinder long axis and the XY plane, as shown in FIGS. 14(*a*)-(*d*). FIGS. 14(*a*)-(*d*) show a 3D Imaging restricted sampling pattern where FIG. 14(*a*) is the sample orientation, FIG. 14(*b*) shows the points required in k-space with end and side views are shown in FIG. 14(*c*) and FIG. 14(*d*), respectively. This takes about 7% of k-space points with a threshold of 0.4%, for sample length/FOV=⅔ in all dimensions.

The method according to another embodiment of the present invention is extended to the $T_2$ mapping SESPI method, where the k-space sampling method according to an embodiment of the present invention is implemented with no special trajectory requirement. In some measurement, such as hybrid-SESPI and SPRITE, care must be exercised in the choice of the k-space sampling pattern, the trajectory, since there are attenuations due to $T_2$ or $T_1$ relaxation. To achieve a proton density image, the k-space origin should be free of these attenuations. The shape of the point spread function is also important for a reasonable blurring in the image domain. In 2D hybrid-SESPI and SPRITE, the required k-space points are grouped into 4 interleaves according to 4 "arms" in the "cross" pattern. In 3D SPRITE, the sampled points are rearranged into 16 or 24 sectors, depending on the required length of interleaves. Each sector occupies a solid angle of $\pi/4$ or $\pi/6$ covering the full solid angle of $4\pi$. The k-space points located within the same interleave are connected in the order of increasing distance from the k-space origin. Then the points are slightly reordered into a smooth curve to minimize gradient switching.

These sampling patterns, with the remaining points set to zero, upon Fourier transformation, yield good quality images with only slight blurring near the corners. The detailed structures are preserved, since the sampling patterns include high frequency components in k-space. The results show that the restricted k-space sampling provides more reliable images, in most cases for rock core plugs, than those from compressed sensing [1].

Methods according to the present invention may be used to image rock samples but are not limited to imaging rock samples. The geometry based restricted sampling method according to certain embodiments of the present invention may be extended to other sample shapes, such as rectangular parallelepipeds, spheres and triangles.

Figure 15:
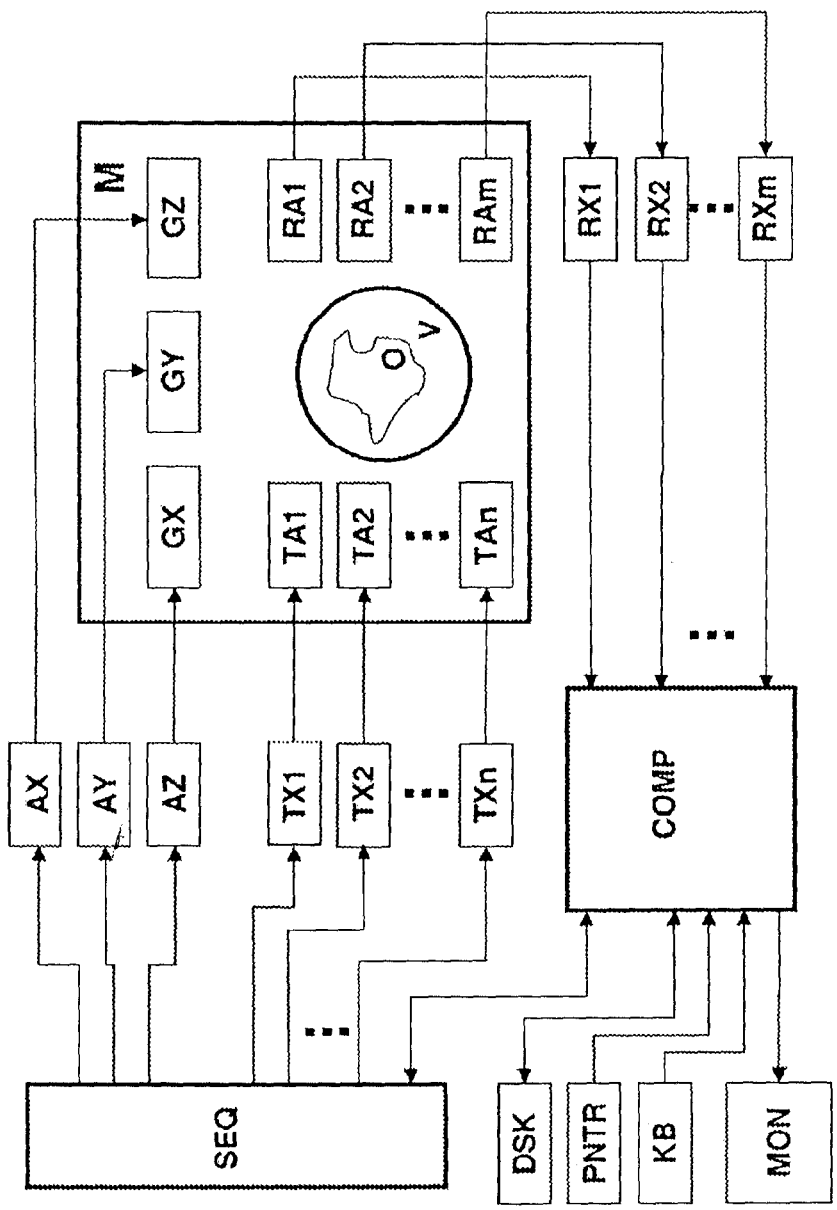

The invention may be implemented in a conventional MRI instrument as a programmed pulse sequence and may be used with an MRI instrument having low field permanent magnets. For example, FIG. 15 schematically shows an MRI measuring system which is suited for performing the inventive method. The system contains a main magnet M for generating the basic magnetic field which is substantially homogeneous and static in a volume under investigation V. Three sets of gradient coils GX, GY, and GZ are introduced into the bore of the main magnet M, which surround the volume under investigation V, and can superpose additional magnetic fields of controllable duration and strength with constant gradients on the basic field. Gradient amplifiers AX, AY, and AZ, which are driven by a sequence control unit SEQ for timely generation of gradient pulses, provide the gradient coils GX, GY, GZ with electric current for generating substantially linear gradient fields.

Several transmitting elements TA1 to TAn are located in the gradient field system, the entirety of which is also called transmitting antenna means. They surround an object under investigation O and are fed by several independent RF power transmitters TX1 . . . TXn. The RF pulses generated by these RF power transmitters TX1 . . . TXn are determined by the sequence control unit SEQ and triggered at the correct time. The transmitting elements TA1 to TAn irradiate RF pulses onto the object under investigation O located in the volume under investigation V (as described in more detail in FIG. 15), thereby exciting the nuclear spins. The resulting magnetic resonance signals are converted into electric voltage signals using one or more RF receiver elements RA1, . . . , RAm, which are then supplied to a corresponding number of receiver units RX1, . . . , RXm. The overall receiver elements RA1, . . . , RAm are also called receiver antenna means that consists of m receiver elements RA1, . . . , RAm. These are also located within the gradient coils GX, GY, GZ and surround the object under investigation O. In order to reduce the expense for equipment, the transmitting and receiver antenna means may also be designed and connected in such a fashion that one or more of the transmitting elements TA1 to TAn are also used for receiving the magnetic resonance signals. In this case, which is not considered in FIG. 18, switching over between transmitting and receiving operation is effected by one or more electronic transmitting-receiver switch points that are controlled by the sequence control unit SEQ. This means that during the RF transmitting phases of the executed RF pulse sequence, this antenna(s) is/are connected to the corresponding RF power transmitter(s) and is/are separated from the allocated receiver channels, while for the receiver phases, the transmitters are separated and the receiver channel is connected. The received signals are amplified by the receiving units RX1 to RXm shown in FIG. 15, and are converted into digital signals using conventional signal processing methods, and passed on to an electronic computer system COMP. In addition to the reconstruction of images and spectra and values derived from the received measured data, the controlling computer system COMP serves to operate the entire MRI measuring system and initiates performance of the pulse sequences through corresponding communication with the sequence control unit SEQ. The user-controlled or automatic execution of programs for adjusting the measuring system properties and/or for generating magnetic resonance images is also provided on this control computer system COMP, as well as the display of the reconstructed images, storage and management of measurement and image data and control programs. In order to perform these tasks, this computer system has at least one processor, one working memory, one computer keyboard KB, one display instrument PNTR, e.g. a computer mouse, one screen MON and one external digital storage unit DSK.

It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertain, and those aspects and modifications are within the scope of the invention.

REFERENCES

[1] T. Wen, One well evaluation in low permeability gas sandstones from Nuclear Magnetic Resonance (NMR) logs, Society of Petroleum Engineers Middle East Unconventional Gas Conference and Exhibition (2011) SPE 140798.
[2] M. O. Amabeoku, J. J. Funk, S. M. Al-Dossary, H. A. Al-Ali, Calibration of permeability derived from NMR Logs in carbonate reservoirs, Society of Petroleum Engineers Middle East Oil Show (2001) SPE 680685.
[3] G. M. Hamada, M. S. Al-Blehed, M. N. J. Al-Awad, Determining Petrophysical properties of low resistivity reservoirs using Nuclear Magnetic Resonance Logs. Society of Petroleum Engineers Annual Technical Conference and Exhibition (1999) SPE 56789.
[4] H. A. Ohen, A. O. Ajufo, Laboratory NMR relaxation measurements for the acquisition of calibration data for NMR Logging tools, Society of Petroleum Engineers Western Regional Meeting (1996) SPE 35683.
[5] C. E. Morriss, R. Freedman, C. Straley, M. Johnston, H. J. Vinegar, P. N. Tutunjian, Hydrocarbon saturation and viscosity estimation from NMR Logging in the Belridge Diatomite, SPWLA 35th Annual Logging Symposium (1994).
[6] S. Menger, M. Prammer, A new Algorithm for analysis of NMR logging data, Society of Petroleum Engineers Annual Technical Conference and Exhibition (1998) SEP 49013.
[7] M. G. Prammer, NMR pore size distributions and permeability at well site, 69th Society of Petroleum Engineers Annual Technical Conference and Exhibition (1994) SPE 28368.
[8] R. Freedman, Processing of data from an NMR logging tool, Society of Petroleum Engineers Annual Technical Conference and Exhibition (1995) SPE 30560.
[9] S. Chen, D. Georgi, S. Fang, J. Salyer, D. Shorey, Optimization of NMR logging acquisition and processing. Society of Petroleum Engineers Annual Technical Conference and Exhibition (1999) SPE 56766.
[10] M. N. Miller, Z. Paltiel, M. E. Gillen, J. Granot, J. C. Bouton, Spin echo magnetic resonance logging: porosity and free fluid index determination, Society of Petroleum Engineers Annual Technical Conference and Exhibition (1990) SPE 20561.
[11] C. S. Poon, R. M. Henkelman, Practical $T_2$ quantification for clinical applications, Journal of Magnetic Resonance Imaging 2 (1992) 541-553.
[12] O. Bieri, K. Scheffler, G. H. Welsch, S. Tratting, T. C. Mamisch, C. Ganter, Quantitative mapping of $T_2$ using partial spoiling, Magnetic Resonance in Medicine 66 (2011) 410-418.
[13] O. Beuf, A. Briguet, M. Lissac, R. Davis, Magnetic resonance imaging for the determination of magnetic susceptibility of materials, Journal of Magnetic Resonance, Series B 112 (1996) 111-118.
[14] B. J. Balcom, R. P. MacGregor, S. D. Beyea, D. P. Green, R. L. Armstrong, T. W. Bremner, Single-point ramped imaging with $T_1$ enhancement. Journal of Magnetic Resonance Series A 123 (1996) 131-134.
[15] L. Li, H. Han, B. J. Balcom, Spin echo SPI methods for quantitative analysis of fluids in porous media. Journal of Magnetic Resonance 198 (2009) 252-260.
[16] O. V. Petrov, G. Ersland, B. J. Balcom, $T_2$ distribution mapping profiles with phase-encode MRI, Journal of Magnetic Resonance 209 (2011) 39-46.
[17] O. V. Petrov, B. J. Balcom, Two-dimensional $T_2$ distribution mapping in porous solids with pure phase encode MRI. Journal of Magnetic Resonance 212 (2011) 102-108.
[18] G. McGibney, M. R. Smith, S. T. Nichols, A. Crawley, Quantitative evaluation of several partial Fourier reconstruction algorithms used in MRI, Magnetic Resonance in Medicine 30 (1993) 51-59.
[19] G. J. Marseille, R. De Beer, M. Fuderer, A. F. Mehlkope, D. Van Ormondt, Nonuniform phase-encode distributions for MRI scan time reduction, Journal of Magnetic Resonance Series B 111 (1996) 70-75.
[20] A. V. Barger, W. F. Block, Y. Toropov, T. M. Grist, C. A. Mistretta, Time-resolved contrast-enhanced imaging with isotropic resolution and broad coverage using an undersampled 3D projection trajectory, Magnetic Resonance in Medicine 48 (2002) 297-305.
[21] M. Lustig, D. Donoho, and J. M. Pauly, Sparse MRI: The Application of Compressed Sensing for Rapid MR Imaging. Magnetic Resonance in Medicine 58 (2007) 1182-1195.

[22] M. Halse, D. J. Goodyear, B. MacMillan, P. Szomolanyi, D. Matheson, B. J. Balcom, Centric scan SPRITE magnetic resonance imaging, Journal of Magnetic Resonance 165(2003) 219-229.

[23] A. A. Khrapitchev, B. Newling, B. J. Balcom, Sectoral sampling in centric-scan SPRITE magnetic resonance imaging, Journal of Magnetic Resonance 178 (2006) 288-296.

[24] R. A. Jones, O. Haraldseth, T. B. Müller, P. A. Rinck, A. N. Oksendal, S-Space substitution: A novel dynamic imaging technique, Magnetic Resonance in Medicine 29 (1993) 830-834.

[25] P. Parasoglou, A. J. Sederman, J. Rasburn, H. Powell, M. L. Johns, Optimal k-space sampling for single point imaging of transient systems, Journal of Magnetic Resonance 194 (2008) 99-107.

[26] P. Parasoglou, D. Malioutov, A. J. Sederman, J. Rasburn, H. Powell, L. F. Gladden, A. Blake, M. L. Johns, Quantitative single point imaging with compressed sensing, Journal of Magnetic Resonance 201 (2009) 72-80.

[27] A. K. Nandi, Quality of signals reconstructed from degraded Fourier transform phase, Electronics Letters 26 18 (1990) 1460-1462.

[28] S. G. Mallat, Multiresolution approximations and wavelet orthonormal bases of $L^2(R)$, Transactions of the American Mathematical Society 315 (1989) 69-87.

[29] I. Daubechies, Ten lectures on wavelets, Society for Industrial and Applied Mathematics, Philadelphia, Pa., 1992.

[30] K. Romanenko, B. J. Balcom, Permeability mapping in naturally heterogeneous sandstone cores by magnetization prepared centric-scan SPRITE, AICHE (2011) accepted, DOI:10.1002/aic.13778.

[31] A. Majumdar, R. K. Ward, Accelerating multi-echo $T_2$ weighted MR imaging: Analysis prior group-sparse optimization, Journal of Magnetic Resonance 210 (2011) 90-97.

[32] H. Y. Carr, E. M. Purcell, Effects of diffusion on free precession in Nuclear Magnetic Resonance experiments, Physical Review 94 (1954) 630-638.

[33] J. Mitchell, T. C. Chandrasekera, L. F. Gladden, Obtaining true transverse relaxation time distributions in high-field NMR measurements of saturated porous media: Removing the influence of internal gradients. Journal of Chemical Physics 132 (2010) 244705.

[34] D. Xiao, B. J. Balcom, Two-dimensional T2 distribution mapping in rock core plugs with optimal k-space sampling, Journal of Magnetic Resonance 220 (2012) 70-78.

We claim:

1. A method of MRI of a sample comprising:
   providing a 2D k space sampling model for a cylindrically-shaped sample, wherein the k-space sampling model is based on a Fourier transform of the shape of the sample and the application of an intensity threshold, and wherein the k-space sampling model defines regions of contiguous k-space data points where high intensity k-space data points are anticipated based on the shape of the sample, where the regions are represented in 2D by a cross pattern in a plane defined by two orthogonal axis of k-space;
   experimentally acquiring k-space data points in the regions; and,
   setting the value of k-space data points outside of the regions to zero.

2. The method of claim 1, wherein the method of experimentally acquiring the k-space data points in the regions is selected from the group consisting of frequency encode methods, phase encode methods and combinations thereof.

3. The method according to claim 1, wherein the sample is a cylindrical rock core plug.

4. The method of claim 1, wherein the ratio of the sample size to the image field of view is approximately ⅔.

5. The method of claim 1, further comprising applying Fourier transform to the acquired k-space data points and the k-space data points set to zero for generating an image of the sample in image space.

6. A method of MRI of a sample comprising:
   providing a 3D k-space sampling model for the a cylindrically shaped sample, wherein the k-space sampling model is based on a Fourier transform of the shape of the sample and the application of an intensity threshold, and wherein the k-space sampling model defines regions of contiguous k-space data points where high intensity k-space data points are anticipated based on the shape of the sample, wherein the regions of contiguous k-space data points are represented in 3D by a thick plane in a plane defined by two orthogonal axes of k-space and a thick line in the direction of the third orthogonal axis;
   experimentally acquiring k-space data points in the regions; and,
   setting the value of k-space data points outside of the regions to zero.

7. The method of claim 6, wherein the method of experimentally acquiring the k-space data points in the regions is selected from the group consisting of frequency encode methods, phase encode methods and combinations thereof.

8. The method according to claim 6, wherein the sample is a cylindrical rock core plug.

9. The method of claim 6, wherein the ratio of the sample size to the image field of view is approximately ⅔.

10. The method of claim 6, further comprising applying Fourier transform to the acquired k-space data points and the k-space data points set to zero for generating an image of the sample in image space.

* * * * *